(12) United States Patent
Popovich et al.

(10) Patent No.: US 8,647,487 B2
(45) Date of Patent: *Feb. 11, 2014

(54) SYSTEM AND METHODS FOR AUTOMATICALLY RECOGNIZING A CONTROL SOLUTION

(75) Inventors: Natasha D. Popovich, Pompano Beach, FL (US); Stephen G. Davies, Tamarac, FL (US)

(73) Assignee: Nipro Diagnostics, Inc., Fort Lauderdale, FL (US)

(*) Notice: Subject to any disclaimer, the term of this patent is extended or adjusted under 35 U.S.C. 154(b) by 93 days.

This patent is subject to a terminal disclaimer.

(21) Appl. No.: 13/025,203

(22) Filed: Feb. 11, 2011

(65) Prior Publication Data

US 2011/0192721 A1 Aug. 11, 2011

Related U.S. Application Data

(63) Continuation of application No. 11/417,225, filed on May 4, 2006, now Pat. No. 7,909,983.

(51) Int. Cl.
*G01N 27/327* (2006.01)
(52) U.S. Cl.
USPC .................................. 204/403.04; 204/403.01

(58) Field of Classification Search
USPC ............... 205/775, 777.5, 778, 779; 204/400, 204/403.01, 403.04, 403.09–403.11
See application file for complete search history.

(56) References Cited

U.S. PATENT DOCUMENTS

| 6,033,866 A * | 3/2000 | Guo et al. .................. 435/14 |
| 6,200,786 B1 * | 3/2001 | Huang et al. ................ 435/132 |
| 6,299,757 B1 * | 10/2001 | Feldman et al. ............. 205/775 |
| 7,909,983 B2 * | 3/2011 | Popovich et al. ............ 205/777.5 |
| 2004/0247562 A1 * | 12/2004 | Lee et al. .................. 424/85.1 |
| 2005/0139469 A1 * | 6/2005 | Davies et al. .............. 204/403.01 |
| 2006/0113187 A1 * | 6/2006 | Deng et al. ................ 204/403.01 |

OTHER PUBLICATIONS

Fletcher et al., The effect of methylene blue, a redox agent on the viability of fusobacterium-nuleatum.*

* cited by examiner

*Primary Examiner* — J. Christopher Ball
(74) *Attorney, Agent, or Firm* — Finnegan, Henderson, Farabow, Garrett & Dunner L.L.P.

(57) ABSTRACT

Methods and devices for automatically distinguishing between a control solution and an actual patient/user sample in a biosensor are provided. The solution is introduced into an electrochemical cell having a working and counter electrode. Electric pulses are applied to the cell and resultant signals are measured. Based on a comparison of the measured signals, a meter can determine whether the sample is a control solution or an actual patient/user sample.

16 Claims, 9 Drawing Sheets

SYSTEM AND METHODS FOR AUTOMATICALLY RECOGNIZING A CONTROL SOLUTION

CROSS-REFERENCE TO RELATED APPLICATION

This application is a continuation of U.S. application Ser. No. 11/417,225, filed May 4, 2006, now U.S. Pat. No. 7,909,983 the entire content of which is incorporated herein by reference.

FIELD OF THE INVENTION

The present invention relates to the field of diagnostic testing and, more particularly, to diagnostic testing systems for measuring the concentration of a substance in a sample.

BACKGROUND OF THE INVENTION

The present disclosure relates to a biosensor system and method for accurately measuring an analyte in a bodily fluid, such as blood, wherein the system comprises a unique process and system for distinguishing between the application of a test control solution and an actual sample. For example, the present disclosure provides a system and method for preventing a biosensor from erroneously identifying a control solution as an actual patient/user sample.

Electrochemical sensors have long been used to detect and/or measure the presence of substances in a fluid sample. For example, sensors have been used to detect the presence of one or more analytes in a fluid. The one or more analytes may include a variety of different substances, which may be found in biological samples, such as blood, urine, tears, semen, feces, gastric fluid, bile, sweat, cerebrospinal fluid, saliva, vaginal fluid (including suspected amniotic fluid), culture media, and/or any other biologic sample. The one or more analytes may be found in nonbiologic samples as well, such as food, water, wine, pool chemistry, soil, gases, and/or any other nonbiologic sample. In the most basic sense, electrochemical sensors comprise a reagent mixture containing at least an electron transfer agent (also referred to as an "electron mediator") and an analyte specific bio-catalytic protein (e.g. a particular enzyme), and one or more electrodes. Such sensors rely on electron transfer between the electron mediator and the electrode surfaces and function by measuring electrochemical redox reactions. When used in an electrochemical biosensor system or device, the electron transfer reactions are transformed into an electrical signal that correlates to the concentration of the analyte being measured in the fluid sample.

The use of such electrochemical sensors to detect analytes in bodily fluids, such as blood or blood derived products, tears, urine, and saliva, has become important, and in some cases, vital to maintain the health of certain individuals. In the health care field, people such as diabetics, for example, have a need to monitor a particular constituent (e.g. glucose) within their bodily fluids. A number of systems are available that allow people to test a body fluid, such as, blood, urine, or saliva, to conveniently monitor the level of a particular fluid constituent, such as, for example, cholesterol, proteins, and glucose. Patients suffering from diabetes, a disorder of the pancreas where insufficient insulin production prevents the proper regulation of blood glucose levels, have a need to carefully monitor their blood glucose levels on a daily, or even more frequent, basis. A number of systems that allow people to conveniently monitor their blood glucose levels are available. Such systems typically include a test strip where the user applies a blood sample and a meter that "reads" the test strip to determine the glucose level in the blood sample. Diligent testing and controlling blood glucose levels by diabetics can reduce the risk of serious damage to the eyes, nerves, and kidneys as well as lower the risks of some forms of cardiovascular disease.

An exemplary electrochemical biosensor is described in commonly-assigned U.S. Pat. No. 6,743,635 ('635 patent) which is incorporated by reference herein in its entirety. The '635 patent describes an electrochemical biosensor used to measure glucose level in a blood sample. The electrochemical biosensor system is comprised of a test strip and a meter. The test strip includes a biosensor formed of a sample chamber, a working electrode, a counter electrode, and fill-detect electrodes. A reagent layer is disposed in the sample chamber. The reagent layer contains an enzyme specific for glucose, such as, glucose oxidase or glucose dehydrogenase, and a mediator, such as, potassium ferricyanide or ruthenium hexaamine. When a user applies a blood sample to the sample chamber on the test strip, the reagents react with the glucose in the blood sample. The meter applies a voltage to the electrodes to cause electrochemical redox reactions. When an appropriate potential is applied between the working electrode and the counter electrode, the electron mediator is oxidized, thereby generating a current that is related to the glucose concentration in the blood sample. The meter measures the resulting current that flows between the working and counter electrodes and calculates the glucose level based on current measurements.

Because of variations inherent in the biosensor manufacturing process, test strips do not perform identically. Therefore, it is necessary to calibrate the measuring instrument, such as, for example a meter, in a lot-specific manner. This is nowadays carried out automatically by means of lot-specific codes that are read by the measuring instrument or are entered into the measuring instrument by the user. The code is then used by the meter software to automatically adjust and calibrate the algorithm used by the meter to evaluate the electrical measurements.

Lot-specific differences are often due to the manufacturing processes and differences in the chemical reagent layer. In addition, measuring instruments are also subject to variations in their measuring accuracy. For example, measurement inaccuracy can result from prolonged or inappropriate storage of the test strips. In addition, inaccuracies can also result from improper meter usage by the operator. Hence, it is necessary to carry out a functional and quality control of the measuring system at regular intervals in order to detect and, if necessary, eliminate calibration errors in the instrument itself. For these purposes, manufacturers of measuring systems offer control liquids for use with a measuring system. The control liquids are usually essentially composed of aqueous, buffered solutions of the subject analyte in a known, predetermined concentration.

The control solutions are most often applied by a user when using a particular meter for the first time, when using a test strip from a new lot for the first time, after the meter has been dropped (or otherwise subject to potential damage), or when the previous results displayed from a sample do not seem to match usual or expected results. A control test can also be performed on a periodic basis. When performing a test with the control solution, most meters require that a user perform a certain initial test protocol, such as entering a specific code, or pressing a particular button or key on the meter. This initial protocol alerts the meter that the following results are indicative of the control solution and not the results of an actual patient sample. Based on the control solution test results, the meter will then properly calibrate its measurement algorithm as necessary to compensate for measurement inaccuracies.

Properly indicating the occurrence of a control solution test is important for the proper operation of the meter as well as for maintaining a proper patient test history. In some meters, the patient's test history, including the time of testing and sample results, is recorded in memory and used as underlying data to warn the user, according to certain preset alert conditions. If a user fails to accurately notify the meter when a control solution test is being administered, the meter will erroneously record the result as a valid patient test result (as opposed to merely a control solution). Such an oversight can lead to a number of problems, such as an inaccurate or incomplete patient record or history being recorded in the meter's memory. In turn, these inaccuracies can potentially lead to a dangerous situation where a doctor erroneously provides a diagnosis based on improper patient information.

Accordingly, there is a need in the field of measuring the concentration of a substance in a sample for a system and method that reduces the potential for improperly designating a control sample as an actual user/patient sample.

SUMMARY OF THE INVENTION

The claimed embodiments disclosed herein relate to systems and methods of for automatically distinguishing between a control solution and an actual patient/user sample in a biosensor.

One embodiment is directed to a system for automatically distinguishing between a control solution and an actual patient/user sample in a biosensor comprising a sample reception region and a reaction reagent system. The reaction reagent system comprises an oxidation-reduction enzyme specific for an analyte, and a first electron mediator capable of being reversibly reduced and oxidized, and a distinction system configured to identify a control solution having a known, predetermined concentration of the analyte and a second electron mediator capable of capable of undergoing an electrochemical redox reaction.

In various embodiments, the system may include one or more of the following additional features: wherein the analyte is glucose; wherein the second electron mediator does not interfere with the measurement of the analyte; wherein the first electron mediator is a ruthenium containing material; wherein the ruthenium containing material comprises hexaamine (III) trichloride; wherein the second mediator is Ferrocene Dicarboxylic Acid; wherein the second mediator is Ferrocenecarboxylic Acid; wherein the second mediator is gentisic acid (2,5-dihydroxybenzoic acid); wherein the second mediator is 2,3,4-trihydroxybenzoic acid; wherein the second mediator is oxidized or reduced in a potential range distinguishable from that of the first mediator; wherein the second electron mediator is oxidized or reduced at a potential having a magnitude at least 0.2 volts greater or less than that used to oxidize or reduce the first electron mediator; and wherein the redox potential of the first electron mediator is different from the redox potential of the second electron mediator.

Another embodiment is directed to a method for automatically distinguishing between a control solution and an actual patient/user sample in a biosensor comprising providing an electrochemical cell comprising a spaced apart working and counter electrodes and a redox reagent system comprising an enzyme specific for an analyte. The method further includes introducing into the reaction cell, a control solution a having a known, predetermined concentration of the analyte, applying a first electric pulse to the reaction cell and measuring a first resulting electrical property of the cell, applying a second electric pulse to the cell and measuring a second resulting electrical property of the cell, comparing the first and second measurements; and determining the presence or absence of a control solution based on the results of the comparison performed.

In various embodiments, the method may include one or more of the following additional features: wherein the analyte is glucose; wherein the first and second electrical properties measured are electrochemical signals comprised of electric current signals obtained through multi-step chronoamperometry; wherein the first and second electrical properties measured are electrochemical signals comprised electric current signals obtained through square wave voltammetry; wherein the first and second electrical properties measured are electrochemical signals comprised of electric current signals obtained through differential pulse amperometry; wherein the first and second electrical properties measured are electrochemical signals comprised of electric current signals obtained through cyclic voltammetry; wherein providing an electrochemical cell comprises providing a first electron mediator capable of being reversibly reduced and oxidized and wherein the control solution includes a second electron mediator capable of capable of undergoing an electrochemical redox reaction; wherein introducing the control solution results in an oxidation or reduction of the first mediator and wherein applying a second electric pulse results in oxidation or reduction of the second mediator; wherein the second electron mediator is oxidized or reduced at a potential having a magnitude at least 0.2 volts greater or less than that used to oxidize or reduce the first electron mediator; wherein the redox potential of the first electron mediator is different from the redox potential of the second electron mediator; wherein the second mediator is Ferrocene Dicarboxylic Acid; wherein the second mediator is Ferrocenecarboxylic Acid; wherein the second mediator is gentisic acid (2,5-dihydroxybenzoic acid); and wherein the second mediator is 2,3,4-trihydroxybenzoic acid.

Another embodiment is directed to a fluid control solution for use in calibrating a biosensor system comprising a known, predetermined concentration of an analyte and an electron mediator capable of capable of undergoing an electrochemical redox reaction.

In various embodiments, the fluid control solution may include one or more of the following additional features: wherein the control solution is configured for use in a biosensor system having an oxidation-reduction enzyme specific for the analyte and a second electron mediator capable of being reversibly reduced and oxidized; wherein the electron mediator of the control solution is oxidized or reduced at a potential having a magnitude at least 0.2 volts greater or less than that used to oxidize or reduce the second electron mediator; wherein the control solution is configured for use in a biosensor system having an oxidation-reduction enzyme specific for the analyte and a second electron mediator capable of being reversibly reduced and oxidized; wherein the redox potential of the electron mediator for the control solution is different from the redox potential of the second electron mediator; wherein the electron mediator is Ferrocene Dicarboxylic Acid; wherein the electron mediator is Ferrocenecarboxylic Acid; wherein the electron mediator is gentisic acid (2,5-dihydroxybenzoic acid); wherein the electron mediator is 2,3,4-trihydroxybenzoic acid; and wherein the analyte is glucose.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one embodiments of the invention and together with the description, serve to explain the principles of the invention.

DESCRIPTION OF THE EMBODIMENTS

Figure 1:
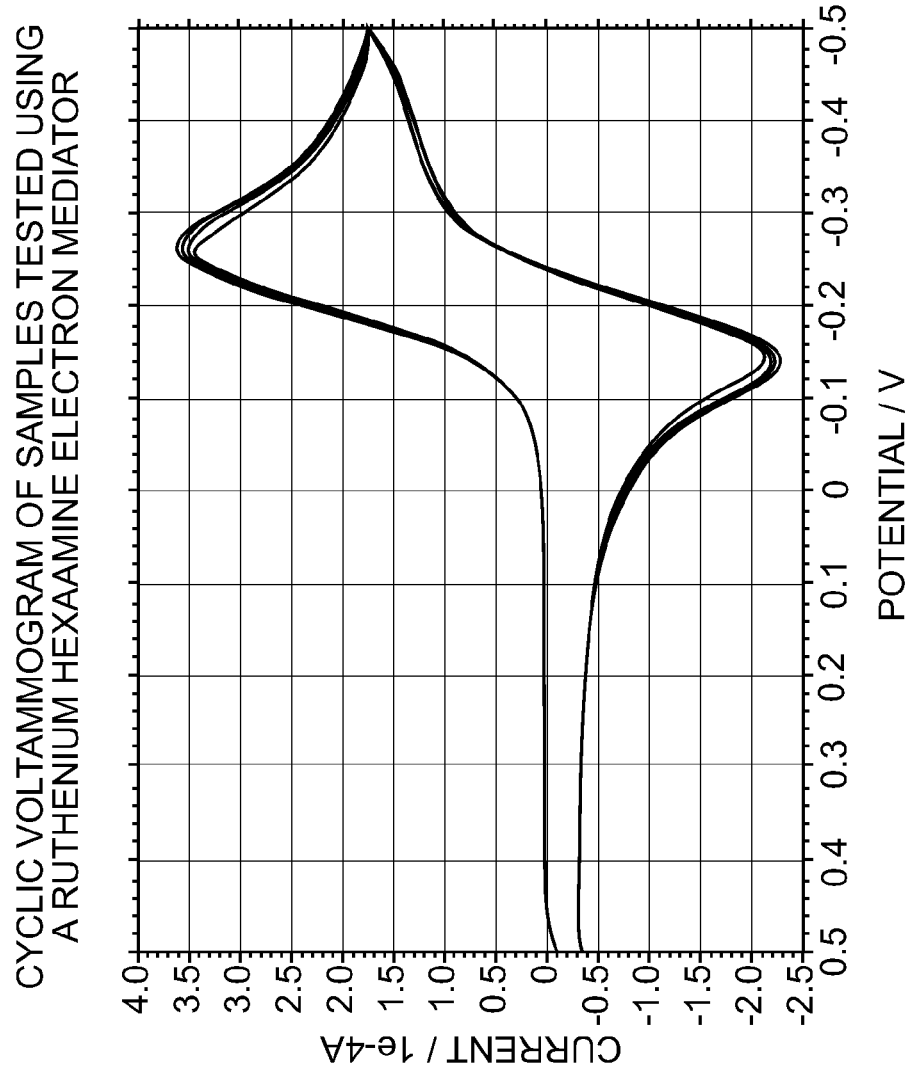
FIG. 1 is a cyclic voltammogram associated with the use of a thin film gold electrode with a ruthenium hexaamine electron mediator.

In accordance with the present disclosure provided herein are electrochemical sensors developed for measuring an concentration of a particular substance, such as an analyte, in a non-homogenous fluid sample, such as in a food product or in a bodily fluid chosen from blood, urine, saliva and tears. At a minimum, the underlying biosensor includes at least one or more electrodes and a reaction reagent system comprising an electron mediator and an oxidation-reduction enzyme specific for the analyte to be measured. In one embodiment, the electron mediator comprises a ruthenium containing material, such as ruthenium hexaamine (III) trichloride.

As used herein, the phrase "working electrode" is an electrode at which the electrochemical oxidation and/or reduction reaction occurs, e.g., where the analyte, typically the electron mediator, is oxidized or reduced.

"Counter electrode" is an electrode paired with the working electrode. A current of substantially equal magnitude and of opposite polarity to the working electrode passes through the counter electrode.

"YSI" or "YSI values" means a particular analyte concentration as determined using a Yellow Springs Instrument glucose analyzer, such as, for example, the YSI model 2300 Stat Plus.

As noted above, the '635 patent describes an exemplary electrochemical biosensor used to measure glucose level in a blood sample. The electrochemical biosensor system is comprised of a test strip and a meter. The test strip includes a sample chamber, a working electrode, a counter electrode, and fill-detect electrodes. A reagent layer is disposed in the sample chamber, and generally covers at least part of the working electrode as well as the counter electrode. The reagent layer contains an enzyme specific for glucose, such as, glucose oxidase or glucose dehydrogenase, and a mediator, such as, potassium ferricyanide or ruthenium hexaamine.

In one example, glucose oxidase is used in the reagent layer. The recitation of glucose oxidase is intended as an example only and other materials can be used without departing from the scope of the invention. For example, glucose dehydrogenase is another enzyme that is used in glucose biosensors. Similarly, while potassium ferricyanide is listed as a possibly mediator, other possible mediators are contemplated. For example, additional mediators include, but are not limited to, ruthenium, osmium, and organic redox compounds. In one embodiment, during a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and displays the calculated glucose level to the user.

Commonly owned co-pending U.S. patent application Ser. No. 11/242,925 (which is incorporated herein by reference in its entirety) discloses the use of ruthenium hexaamine as another potential mediator. When ruthenium hexaamine [Ru(NH$_3$)$_6$]$^{3+}$ is used, the glucose oxidase initiates a reaction that oxidizes the glucose to gluconic acid and reduces [Ru(NH$_3$)$_6$]$^{3+}$ to [Ru(NH$_3$)$_6$]$^{2+}$. In the case of glucose dehydrogenase, the enzyme oxidizes glucose to glucono-1,5-lactone, and reduces [Ru(NH3)6]$^{3+}$ to [Ru(NH3)6]$^{2+}$. When an appropriate voltage is applied to the working electrode, relative to the counter electrode, the electron mediator is oxidized. For example, ruthenium hexaamine [Ru(NH$_3$)$_6$]$^{2+}$ is oxidized to [Ru(NH$_3$)$_6$]$^{3+}$, thereby generating a current that is related to the glucose concentration in the blood sample.

The systems and methods of the present application rely on electron transfer between the electron mediator and the electrode surfaces and function by measuring electrochemical redox reactions. As noted above, these electron transfer reactions (such as the ferrocyanide or ruthenium hexaamine reactions described above) are transformed into an electrical signal that correlates to the concentration of the analyte being measured in the fluid sample. More particularly, the electrical signal results from the application of particular electrode potential input (comprised of a single constant pulse or distinct separate pulses at more than one potential) at the working electrode relative to a counter electrode.

The pulse or pulses are applied to the cell at a particular predetermined potential relative to the redox potential of the particular strip mediator used. As is known in the art, the redox potential of a substance is a measure (in volts) of the substances affinity for electrons (i.e. the substance's electronegativity) compared with hydrogen, which is set at zero. Substances more strongly electronegative than (i.e., capable of oxidizing) hydrogen have positive redox potentials. Substances less electronegative than (i.e., capable of reducing) hydrogen have negative redox potentials. One way to determine the particular redox potential of a substance is by cyclic voltametry. FIG. 1, for example is a cyclic voltammogram associated with the use of a thin film gold electrode with a ruthenium hexaamine electron mediator. As seen in FIG. 1, the ruthenium hexaamine substance exhibits a negative redox potential of about −0.2 volts vs Ag/AgCl reference electrode in pH 7.25 phosophate buffer solution.

Figure 2:
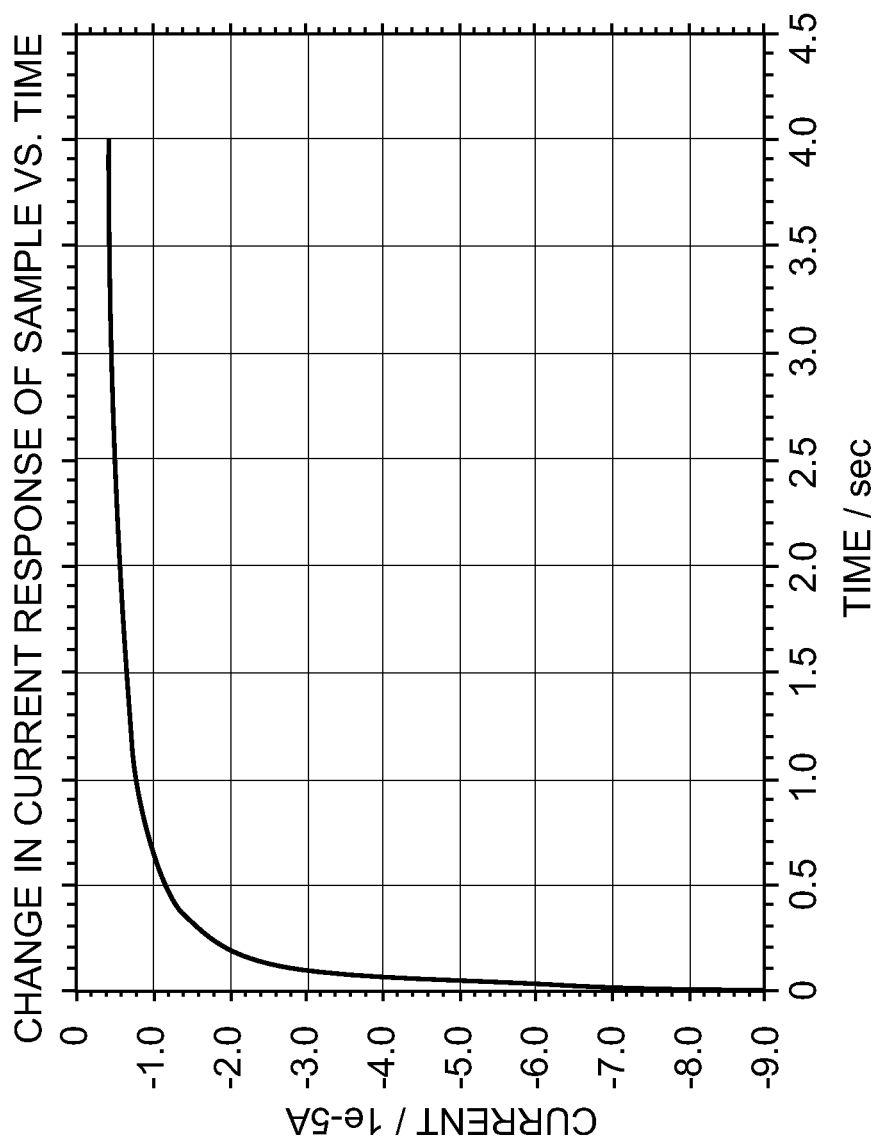
FIG. 2 is a graph depicting the change in current response over time during the application of an input voltage pulse in a glucose measurement.

Accordingly, where the desired electron transfer reaction is a reduction of the mediator, for example, a negative voltage pulse well negative of the redox potential is applied. Conversely, where the desired electron transfer reaction is an oxidation of the mediator, a positive voltage pulse well positive of the redox potential is applied. The particular electrode potential input into the cell results in an electric signal in the form of a current-time transient. In other words, the final concentration measurement is based on the particular current-time transient (also known as the amperometric current response) obtained as a result of applying a particular voltage potential to the cell (i.e. between the working and counter electrodes) and observing the change in current over time between the working and counter electrodes. FIG. 2, for example, is a graph depicting the change in current response over time during the application of an input voltage pulse in a blood sample measurement.

As noted above, one example of a mediator is ruthenium hexaamine. In one embodiment, once a fluid sample, such as a patient's blood sample, is applied to a sample chamber of a test strip, a voltage pulse is applied to the working electrode, relative to the counter electrode, in order to oxidize the ruthenium. In one embodiment, the pulse is applied at a potential of 0.3 volts, well positive of the redox potential depicted in FIG. 1, thereby completely oxidizing the mediator to $[Ru(NH_3)_6]^{3+}$ and generating a current that is related to the glucose concentration in the blood sample.

The particular voltage level applied is carefully selected to assure that the desired redox reaction takes place. The factors taken into account in selecting the particular applied voltage level include the materials of the different electrode components in the reaction cell and the particular redox potential of mediator substance.

The same underlying redox reaction response described above for determining an underlying analyte level is used in the systems and methods described herein to distinguish between a calibration control solution and an actual patient/user fluid sample. As noted above, control liquids are usually essentially composed of aqueous, buffered solutions of the subject analyte in a known, predetermined concentration. In the present system and method, a predetermined substance with known properties is provided within the control solution. In one embodiment, a system and method of distinguishing a control solution from a fluid sample has been developed based on the addition of a secondary redox probe ("SRP") into the control solution. This SRP is a substance that is either not present in a normal analytic sample, or present in readily distinguishable concentration. For purposes of this disclosure, "redox probe" means a substance capable of being oxidized or reduced. The primary redox probe refers to the particular mediator substance associated with the underlying analyte (or other sample component of interest), such as, for example, the ruthenium hexaamine described above.

The particular secondary redox probe can comprise an additional electron mediator substance provided in the control solution and capable of undergoing an electrochemical redox reaction. Accordingly, in the same manner as the ruthenium hexaamine mediator mentioned above, the secondary redox probe substance generates a current in response to the application of a voltage pulse. The secondary redox probe, however, differs from the ruthenium hexaamine (i.e. the primary redox probe), or the alternative primary mediators cited above, in that the secondary redox probe exhibits a significantly different redox potential. For example, the secondary redox probe of the control solution should have a redox potential that does not overlap with the redox potential of the primary probe. Therefore, when a first predetermined voltage level is applied to the reaction cell, the primary redox probe is either completely reduced or oxidized as desired, but not the secondary probe. Next, when a second voltage level is applied to the reaction cell, the secondary redox probe is completely reduced or oxidized as desired.

The current (amperes) response signal produced from the primary redox probe is indicative of the underlying substance being measured, such as glucose concentration (in the case of the ruthenium mediator). Conversely, the electrochemical current response signal produced by an oxidation or reduction of the SRP will be a function of the concentration of the SRP substance in the control solution. Therefore, the existence of a particular current response following the application of a voltage level known to either oxidize or reduce an SRP will expressly alert an underlying meter that the instant sample is a control solution and not an actual user/patient sample.

One important point to note is that the SRP need not be completely oxidized or reduced in this technique. It is satisfactory to merely cause enough oxidation or reduction by means of applied potential in order to generate a current response that makes possible a distinction between a sample with an SRP and one without an SRP.

Some of the classes of compounds that could function as a SRP include transition metal complexes, organometallics, organic dyes and other organic redox-active molecules. The following is an exemplary list of characteristics for the SRP. Although preferred, it is not required that the SRP exhibit all of the following characteristics.

The SRP should not interfere with the glucose measurement (i.e., limited interaction with the enzyme, mediator, or glucose).

The SRP should be oxidized or reduced in a potential range that can be easily distinguished from that of the mediator.

The SRP should be soluble in the control solution.

The SRP should be stable in the control solution.

For an electrochemically active compound to be useful as an SRP, it should have a potential distinctly different from the primary mediator, but not so extreme that measuring it would result in excess background interference. For example, when ruthenium hexaamine is used as the mediator, there are two preferable (but not required) 'windows' in the potential range for the SRP. In an oxidation based approach, one of the windows is from about 0.3 to approximately 1V. The second window is the reduction-based technique, and extends from approximately −0.15V to −0.6V. It is important to remember that the numbers cited here are only for a very specific example, and should not be construed as a general rule. There may be cases where an SRP that has a peak at 0.2V, or at other magnitudes, would be perfectly acceptable. The actual range of the windows is dependent on the potential required for the primary measurement.

It is also important to note that not all SRPs may be appropriate for all glucose levels. For instance, Ferrocene Dicarboxylic Acid was found to be more appropriate for control solutions containing low or nominal amounts of glucose, whereas Gentisic Acid may be better suited for high glucose controls. The actual application of each will become apparent to those skilled in the art.

Beyond the scope of potential ranges and a preference for avoiding interference with the primary measurement, there are few restrictions on what exactly can be used as an SRP. This enables the use of a wide variety of substances, including, but not limited to: simple organics, macromolecules, functionalized microbeads, transition metal complexes, and simple ions. The SRP should be a substance that for a given potential level in volts known to either oxidize or reduce the SRP, will not generate a similar current-time transient in the true sample measurement. Accordingly, the SRP should be chosen specifically for a distinction demonstrated between the SRP and the true sample at the same applied voltage potential.

The SRP is used during a sample measurement by applying a two-step potential waveform. In the first step, the signal of the primary probe is measured on the working electrode in the standard manner. After this initial pulse, a second, different potential pulse, is applied to the working electrode. This second pulse is designed to measure the signal of the Secondary Redox Probe ("SRP"). The pulses can be either negative potential (reduction), or positive potential (oxidation). The preferred type of SRP depends on the primary probe used. In the case of the sensors using an oxidation approach to quantify the initial concentration level, an oxidation-based SRP approach is advantageous in that an oxidation-based SRP is easier to implement than the reduction SRP because the primary measurement step is the same as the SRP detection step, thus allowing the SRP measurement to occur on the same set of electrodes as that used by the primary measurement.

The use of an oxidation based SRP therefore obviates the need to use the fill detect electrodes to form a four-electrode system (required for a reduction based approach), because this simplifies meter design and provides other advantages as well.

In the case of oxidation, the two-step potential approach could be utilized. In this case, the measurement could be conducted using the anode as the working electrode. The first potential step would establish a current baseline for the primary measurement. The potential would then be increased to a higher magnitude required for oxidation of the SRP.

Naturally, where the sample includes no SRP substance, the second potential level applied will not result in a signal characteristic of the SRP being present. This will indicate to the attached meter device that the sample is not a control solution, as no natural sample matrix should have the characteristic signal intensity that the control solution exhibits by virtue of the SRP substance. Accordingly, when an SRP is added to a control solution, a predetermined reaction response to the second applied input voltage can be used to distinguish between a control solution sample having the SRP and a sample solution without the SRP (e.g. a patient's actual blood sample).

Figure 3:
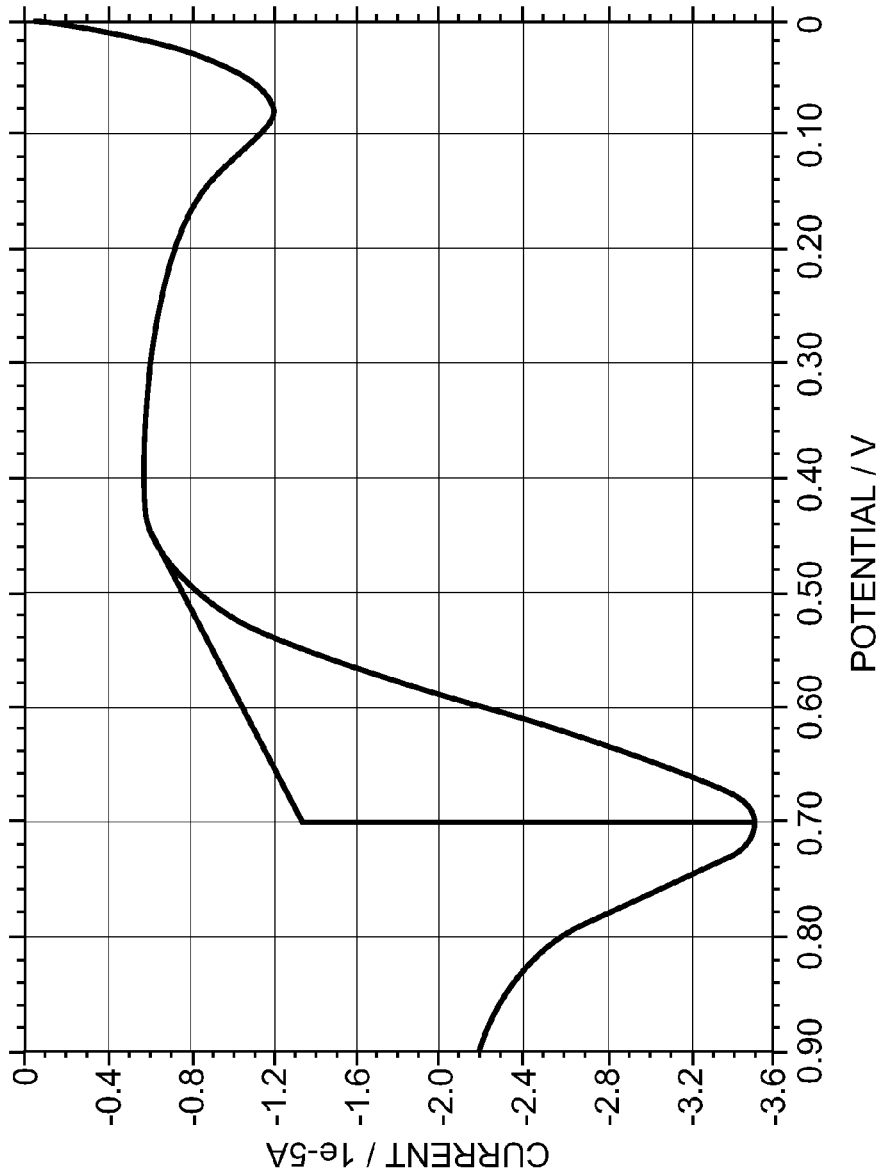
FIG. 3 is a linear sweep voltammogram associated with an electron mediator comprised of Ferrocene Dicarboxylic Acid, according to an embodiment of the present disclosure.

Turning to FIG. 3 one example of an SRP is represented. FIG. 3 depicts a linear sweep voltammogram associated with another potential SRP electron mediator, according to an embodiment of the present disclosure. FIG. 3 depicts a linear sweep voltammogram of the substance Ferrocene Dicarboxylic Acid. The linear sweep voltammogram depicts the response of Ferrocene Dicarboxylic Acid measured with an actual blood sample (i.e. in actual testing conditions). Comparing FIG. 3 and FIG. 1 demonstrates that Ferrocene Dicarboxylic Acid has at least an oxidation peak (e.g. at approximately 0.7 volts) significantly different from that of the ruthenium hexaamine mediator. Therefore, when a ruthenium mediator is used as the primary probe, an SRP of Ferrocene Dicarboxylic Acid will be more easily distinguishable from the primary probe in an oxidation-based measurement. Therefore, during a measurement, the ruthenium hexaamine mediator can be oxidized after the application of a first potential pulse and the Ferrocene Dicarboxylic Acid mediator can be oxidized later after the application of a second, different-potential pulse. As an alternative, Ferrocene carboxylic Acid could be used as an SRP.

Figure 4:
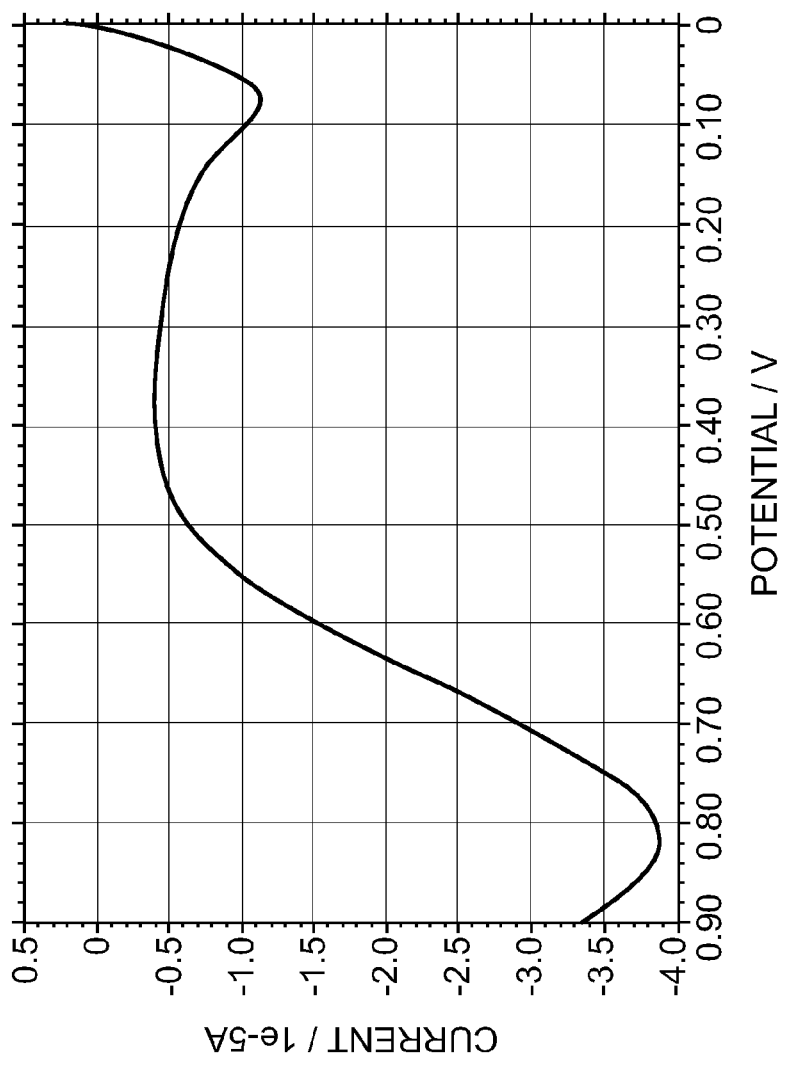
FIG. 4 is a linear sweep voltammogram associated with an electron mediator comprised of Gentisic Acid (2,5-dihydroxybenzoic acid), according to an embodiment of the present disclosure.

Turning to FIG. 4, another example of an SRP is represented. FIG. 4 is a linear sweep voltammogram associated with another potential SRP electron mediator, according to an embodiment of the present disclosure. FIG. 4 depicts a linear sweep voltammogram of the substance Gentisic Acid (2,5-dihydroxybenzoic acid). Comparing the Gentisic Acid peak (the leftmost peak), to the Ruthenium peak (the right peak) demonstrates that Gentisic Acid has at least an oxidation peak (e.g. at approximately 0.81 volts) significantly different from that of the ruthenium hexaamine mediator. Therefore, when a ruthenium mediator is used as the primary probe, an SRP of Gentisic Acid will be more easily distinguishable from the primary probe in an oxidation based measurement. Therefore, during a measurement, the ruthenium hexaamine mediator can be oxidized after the application of a first potential pulse and the Gentisic Acid mediator can be oxidized later after the application of a second different potential pulse. The foregoing voltammograms successfully demonstrate the use of simple organics and transition metal compounds as SRPs.

Concentration of the SRP used is dependent on the specific SRP in question. Many times, the concentration is limited by specific attributes of the SRP or the chemistry. For instance, the SRP may only be soluble to a certain concentration, or it may start to affect the primary measurement at higher concentrations. Also important to note is the voltage used to measure the SRP. An SRP that demonstrates a very intense signal may only require that a small amount be added to observe an adequate signal. For the purposes of the SRPs mentioned in this embodiment, 10-20 mM of SRP mixed into the control solution seems to be sufficient to create an adequate signal without unwanted side effects such as interference with the primary measurement.

A desirable quality for an SRP is that it have redox potential different from that of the primary redox probe. Therefore, the lower boundary for the magnitude of a particular SRP candidate's redox potential for any particular system would be the potential at which the primary probe is measured. In the SRP method, the second pulse potential is carefully selected. It is advantageous to use an SRP substance with as low a redox potential magnitude as possible for a given measurement. The reasoning for this is that at lower redox potential magnitudes, less background signal can be expected. Therefore, the resultant response is less likely to be erroneous due to the effect of unintended redox reactions occurring. Unintended reactions can occur where the potential applied to the sensor system results in unintended oxidation (or reduction in a reduction based approach) of additional components within the control solution. In addition, water in the control solution, for example, can be partially oxidized at exceedingly high potentials.

Additionally, this test can be qualitative, as opposed to a quantitative one, with a simple binary result. Either the sample is control solution, or it is not. Therefore, by adding enough SRP to give an intense signal, it is easy to distinguish between control solution and an actual sample. As noted above, a desirable quality for an SRP substance is that it have a redox potential different from that of the primary redox probe. Therefore, the lower boundary for the magnitude of a particular SRP candidate's redox potential for any particular system would be the potential at which the primary probe is measured.

In another embodiment, the systems and methods of the current application can be combined with those described in commonly owned co-pending U.S. patent application Ser. No. 11/401,458, filed Apr. 11, 2006 (which is incorporated herein by reference in its entirety). In that application, an SRP substance is provided in the actual strip chemistry in order to determine, and account for, the particular hematocrit level of a patient's blood sample. Accordingly, in sensor systems and methods that use an SRP substance to both distinguish a control solution as well as determine hematocrit correction, additional considerations may affect the selection of the potentials applied to a reaction cell during measurement (e.g. interferants present in the patient fluid sample).

As noted in co-pending U.S. patent application Ser. No. 11/401,458, biological fluids, such as, for example, blood, are very complex matrices, and many interferants may be present. These interferants may cause a shift in the SRP signal, which would lead to an erroneous hematocrit correction. Therefore, in such a combined system, it is advantageous to use an SRP substance with as low a redox potential magnitude as possible for a given measurement. The reasoning for this is that at lower redox potential magnitudes, less of the possible pool of interferants undergo redox reactions. Therefore, the resultant response is less likely to be erroneous due to the effect of unintended redox reactions occurring in the interferants.

Figure 5:
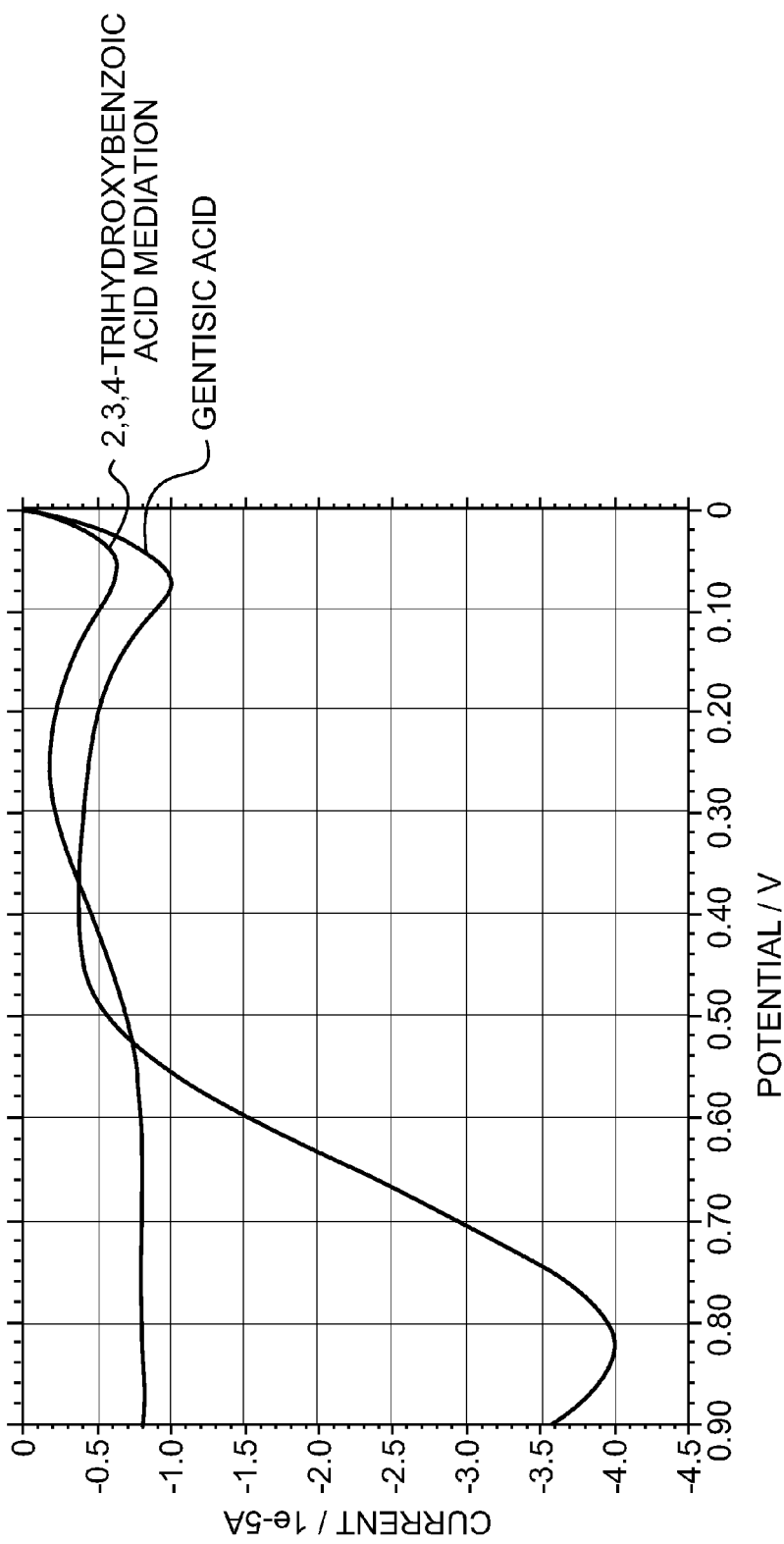
FIG. 5 depicts two linear sweep voltammograms, comparing the Gentisic Acid electron mediator of FIG. 4 with another electron mediator comprised of 2,3,4-trihydroxybenzoic acid, according to an embodiment of the present disclosure.

For purposes of exposition, two oxidation-based SRP substances are compared in FIG. 5. In FIG. 5, one SRP is Gentisic Acid, disclosed previously in FIG. 4. The other is 2,3,4-trihydroxybenzoic acid, a derivative of Gentisic Acid. These two SRPs are structurally similar, but 2,3,4-trihydroxybenzoic acid has a lower redox potential. The linear sweep voltammograms of FIG. 5 show two blood samples, one containing Gentisic Acid chemistry (the curve exhibiting a Y-axis value of about $-3.4 \times 10^{-5}$ Amperes at a potential of 0.9 Volts), and one containing 2,3,4-trihydroxybenzoic acid chemistry (the curve exhibiting a Y-axis value of about $-0.7 \times 10^{-5}$ Amperes at a potential of 0.9 Volts). Differences in magnitude of the peaks should be ignored, as the scan rate is five times as slow for the 2,3,4-trihydroxybenzoic acid sweep, resulting in lower magnitude signal. An examination of FIG. 5 reveals that 2,3,4-trihydroxybenzoic acid has a redox peak near 0.63 V, while gentisic acid has a peak near 0.83 V. This 0.2 V difference in potential can be significant. A chronoamperometric examination of the background signal can reveal the difference in redox peaks.

Figure 6:
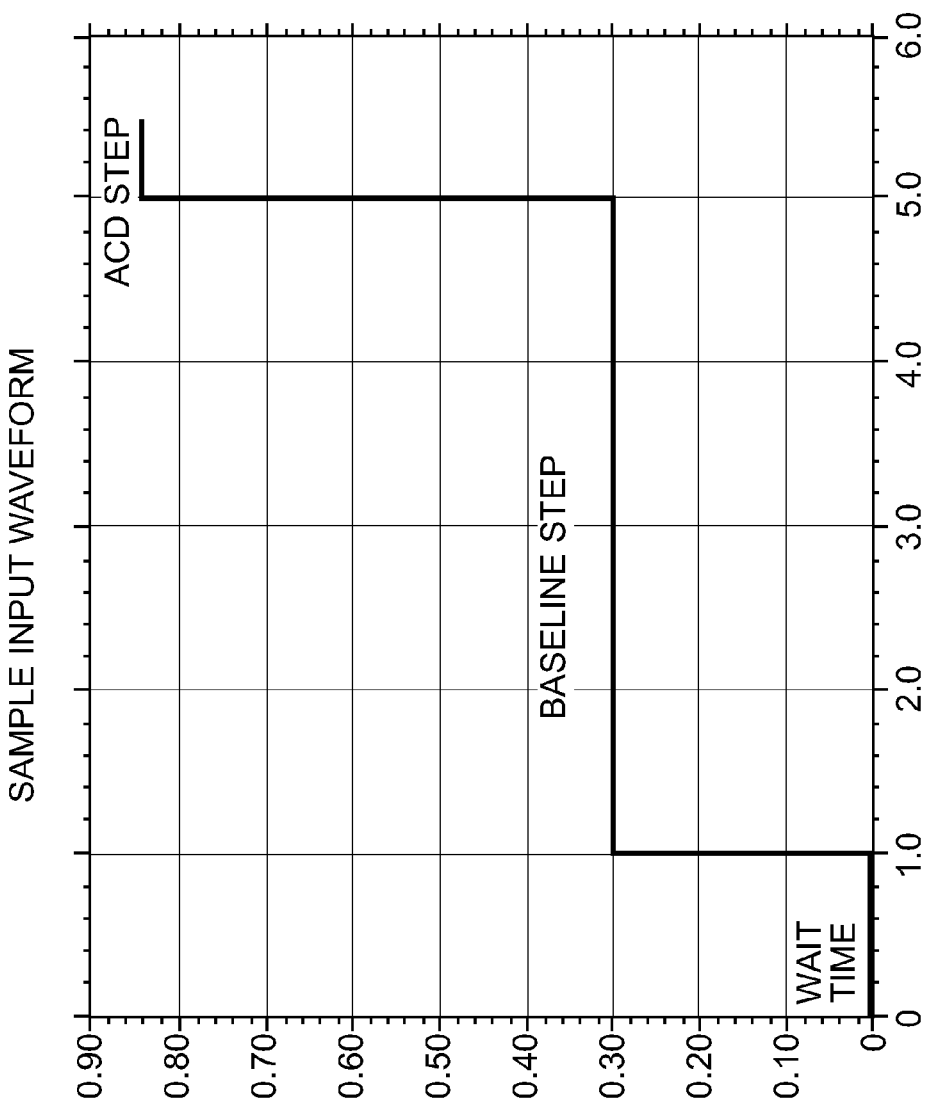
FIG. 6 depicts a particular potential input waveform applied at the working electrode relative to a counter electrode, according to an embodiment of the present disclosure.

In the system and methods of the present application, the control solution having an SRP is clearly distinguishable from a true sample. Accordingly, the underlying meter electronics could be programmed to recognize, and distinguish between, when a control solution measurement was taking place and when a true patient/user sample was being measured. One method of alerting a meter to the differences between a control solution and a true sample is achieved through an input waveform having a shift in applied voltage. FIG. 6 depicts a particular potential input waveform applied at the working electrode relative to a counter electrode. As will be described in more detail below, the current time transients resulting from the application of the input waveform of FIG. 6 result in a signal used to distinguish a control solution from a true sample.

As seen in FIG. 6, after one second of wait time, a first pulse of 0.3 volts is applied for four seconds. A current response measurement is made at the end of the first pulse (i.e. at the 5.0 second time in the plot). After the first 4 second pulse, a second pulse of approximately 0.85 volts was applied. Although less than one second is illustrated, the length of the second pulse can be up to 4 seconds or longer depending on reaction dynamics. The actual measurement during the second pulse, however, is performed at 0.1 seconds after the start of the second pulse, or t=5.1 seconds in the plot of FIG. 6. A change in the current response signal is then obtained by measuring the difference in signal value at 5.1 seconds and subtracting it from the signal at 5.0 seconds. There is no slope correction required in this measurement.

Note that in the previous example, the times used are specific to that sample, and are not intended to limit scope. SRP measurement can occur at any point after the second pulse begins. Thus, in the above example, the SRP could be measured at T=5.01 s, for example. Equally as valid, it could be measured at T=5.5 s, or even at T=7.5 s, if the test time was that long. This is clearly shown in FIG. 7, where the SRP-doped sample is clearly distinguishable across the SRP measurement step. In the interest of reducing time for the user, the test time should be as short as possible without adding cost or complexity to the meter.

The voltage level of the first pulse is predetermined in order to adequately oxidize or reduce the particular electron mediator associated with the underlying constituent measured. For example, the voltage of 0.3 volts is selected where the mediator is the ruthenium hexaamine described above. The voltage level of the second pulse is pulse is predetermined in order to adequately oxidize or reduce the particular electron mediator of comprised of the SRP substance. For example, the voltage of 0.85 is selected in order to oxidize the SRP substance of Gentisic Acid provided in a test control solution according to the present application.

Figure 7:
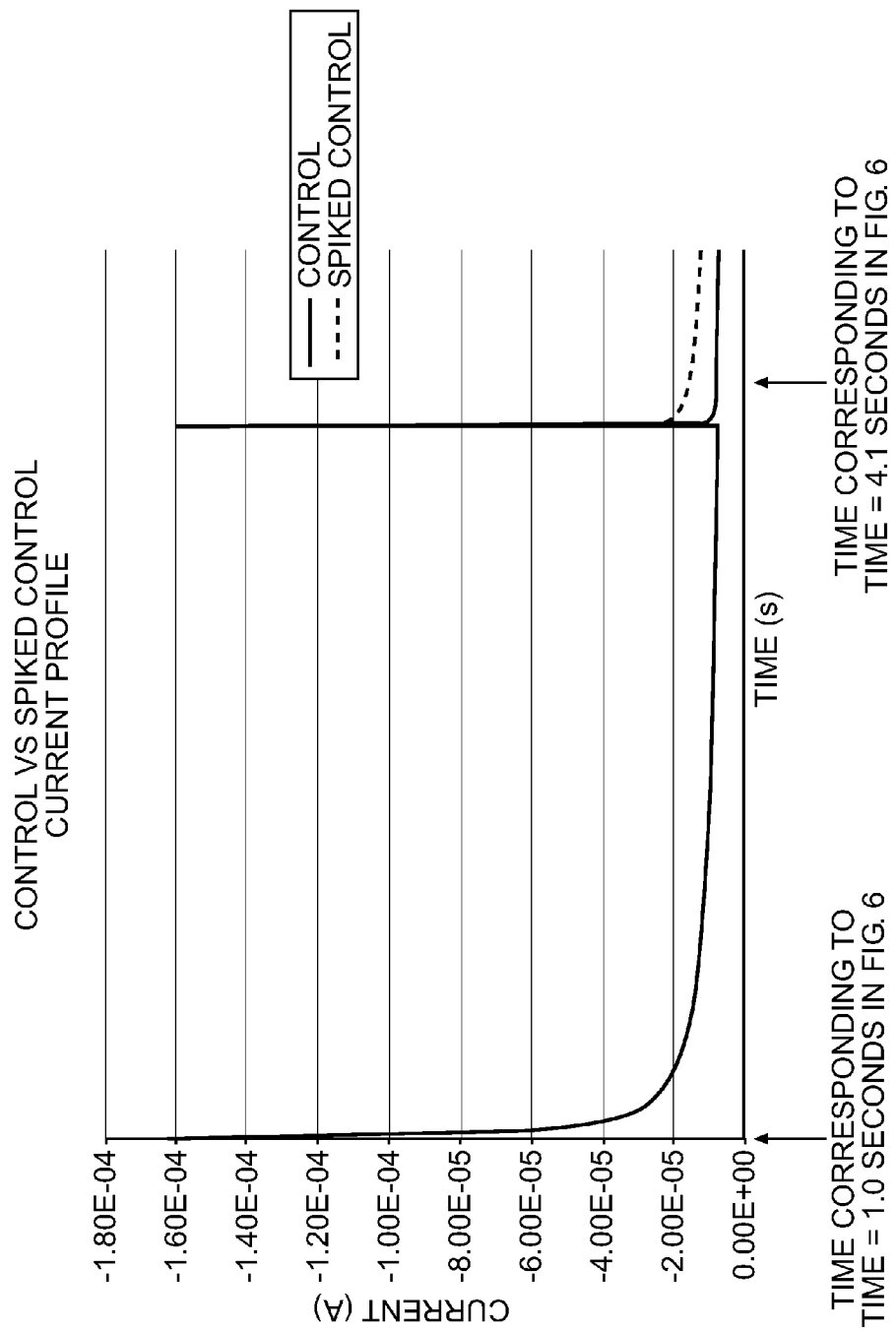
FIG. 7 is a graph depicting the change in current response over time during the application of the input waveform of FIG. 6 with regard to two differing control solutions.

To illustrate the distinction system proposed in this application, the waveform of FIG. 6 was applied to a number of samples, such as, for example, a control solution without the SRP, a control solution with the SRP, and a true sample (e.g. a patient's blood, saliva, or urine). FIG. 7 depicts the current time transient responses of two samples. A first sample is comprised of a standard aqueous, buffered, control solution having a known, predetermined glucose concentration and is depicted by a solid line in FIG. 7. A second sample is comprised of an aqueous, buffered, control solution having a known, predetermined glucose concentration as well as a predetermined SRP component concentration and is depicted by a dashed line in FIG. 7. More particularly, the second type of sample in FIG. 7 includes the SRP comprising Gentisic Acid. The two samples were each subjected to the same input waveform of FIG. 6. The two arrows illustrated along the X-axis of FIG. 7 depict the time corresponding to the input waveform of FIG. 6.

As seen in FIG. 7, both samples exhibited relatively the same current response signal in reaction to the first pulse (i.e. the glucose measurement step). Looking at the time 4.1 (0.1 seconds after the onset of the pulse of 0.85 volts from the input waveform of FIG. 6, designated by the arrow on the left portion of the chart), first sample exhibited little or no relative change from the signal as measured immediately before the application of the pulse increase at time 4.0 seconds. By contrast, the second samples clearly exhibited a higher magnitude (i.e. more negative, further away from the X-axis) amp level current response signal. As set forth above, the first sample was comprised of the standard aqueous, buffered, control solution having a known, predetermined glucose concentration and the second sample was comprised of the same control solution with the addition of the Gentisic Acid SRP. Accordingly, the solution marked with the SRP, depicted in dashed lines in FIG. 7, was easily distinguished from the solution having no SRP component.

Figure 8:
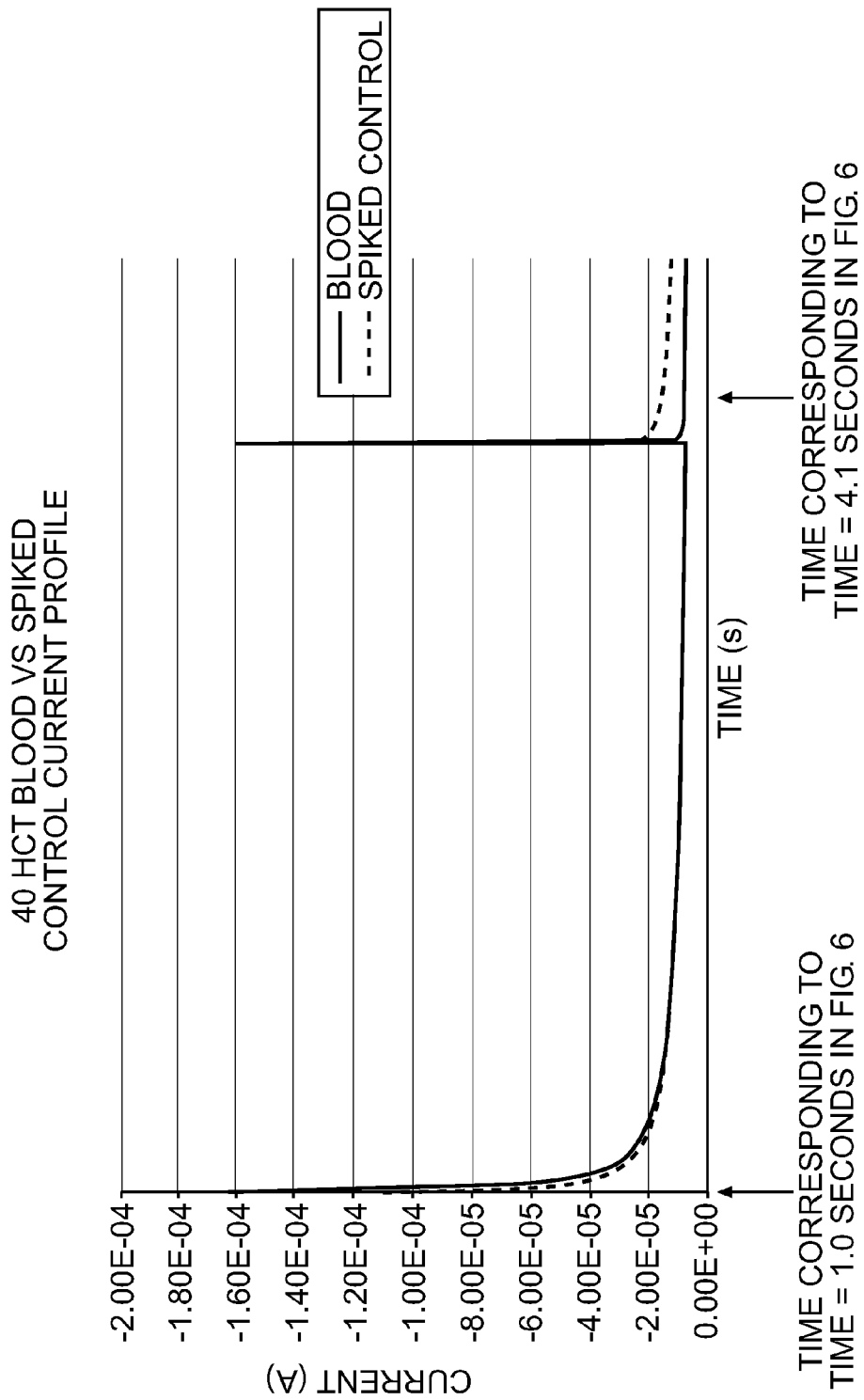
FIG. 8 is a graph depicting the change in current response over time during the application of the input waveform of FIG. 6 with regard to one actual fluid sample and one control solution.

FIG. 8 also depicts the current time transient response of two samples. Each of the two samples is depicted with its own response curve. The two samples were each subjected to the same input waveform of FIG. 6. The two arrows illustrated along the X-axis of FIG. 8 depict the time corresponding to the input waveform of FIG. 6. The first sample was comprised of an actual patient blood sample having a known glucose concentration, depicted by a solid line in FIG. 8. The second sample was comprised of an aqueous, buffered, control solution having the same, predetermined glucose concentration as the blood sample, as well as a predetermined SRP component concentration, depicted by dashed lines in FIG. 8. More particularly, the second sample in FIG. 8 includes the SRP comprising Gentisic Acid.

As seen in FIG. 8, the two samples exhibited relatively the same current response signal in reaction to the first pulse (i.e. the glucose measurement step). Looking at the time 4.1 (0.1 seconds after the onset of the pulse of 0.85 volts from the input waveform of FIG. 6, designated by the arrow on the left portion of the chart), the first sample exhibited little or no relative change from the signal as measured immediately before the application of the pulse increase at time 4.0 seconds. By contrast, the second sample clearly exhibited a higher magnitude (i.e. more negative, further away from the X-axis) amp level current response signal. The first sample was comprised of an actual patient blood sample having a known glucose concentration. The second sample was comprised of the control solution with the addition of the Gentisic Acid SRP. Just as exhibited in the plot of FIG. 7 with regard to the two different control solutions, the solution marked with the SRP in FIG. 8 was easily distinguished from the blood sample, which obviously had no SRP component.

One illustrative algorithm for distinguishing the application of a true patient sample from a control solution including the SRP, would be a simple threshold test. For example, if the current response signal at 4.1 seconds is greater than the current response signal at 4.0 seconds by a certain threshold amount or percentage, then the sample is control solution. This type of algorithm is validated by the values depicted in Table 1 below.

TABLE 1

| Control (10−5 A) | Control w/ ACD Marker (10−5 A) | 40HCT Blood (10−5 A) |
|---|---|---|
| 0.08552 | 0.92834 | 0.0995 |

As explained above, the system and methods of the current application can be used in combination with those described in commonly owned co-pending U.S. patent application Ser. No. 11/401,458, filed Apr. 11, 2006. In such a combined system, the SRP is added to both the chemistry of the biosensor and the control solution formulation. When a true patient sample is added, the SRP detects hematocrit. When a control sample is added, the additional SRP present in the control solution can be measured through several methods. The first is a direct measurement comparison, similar to the threshold test described above. Another approach is to first perform the hematocrit measurement calculation as normal. With the additional SRP present in the control solution, the output of this calculation is significantly different than an output that would result from a true patient sample, (i.e. well above or below the range of values that would be derived from a true patient sample).

In yet another embodiment, the SRP substance need not be added to the control at all, but instead to the strip chemistry itself. This technique is explained in detail in commonly owned co-pending U.S. patent application Ser. No. 11/401,458, filed Apr. 11, 2006. In this technique, the SRP is added to the strip chemistry of the sensor. The measurement calculation is performed as described in the embodiments of application Ser. No. 11/401,458. Where the SRP substance is only present in the strip chemistry, such a configuration can also be modified to distinguish between a control solution (and in particular a control solution without any SRP substance) and a true patient sample. In such a system, the important consideration is the viscosity of the control solution. A control solution with low viscosity will return a reading that is indicative of extremely low hematocrit blood, thereby allowing the meter to determine that a sample is in fact a control solution and not a blood sample (i.e. there is a determination that the calculated hematocrit level of the sample is so low such that it could not represent a true patient blood sample). Conversely, a control solution with high viscosity will return a reading that is indicative of unnaturally high hematocrit blood, thereby signaling that the sample present can only be a control solution and not a true patient blood sample.

Table 1 depicts the average value based on the difference between the current measurement at time 4.0 and the current measurement at time 4.1 with regard to three types of samples. The first column depicts the average difference value in amps for the samples comprised of the standard control solution without the SRP marker. The second, middle column depicts the average difference value in amps for the samples comprised of the control solution with the SRP marker component added. Finally, the third column depicts the average difference value in amps for the samples comprised of blood having a 40% hematocrit level.

Figure 9:
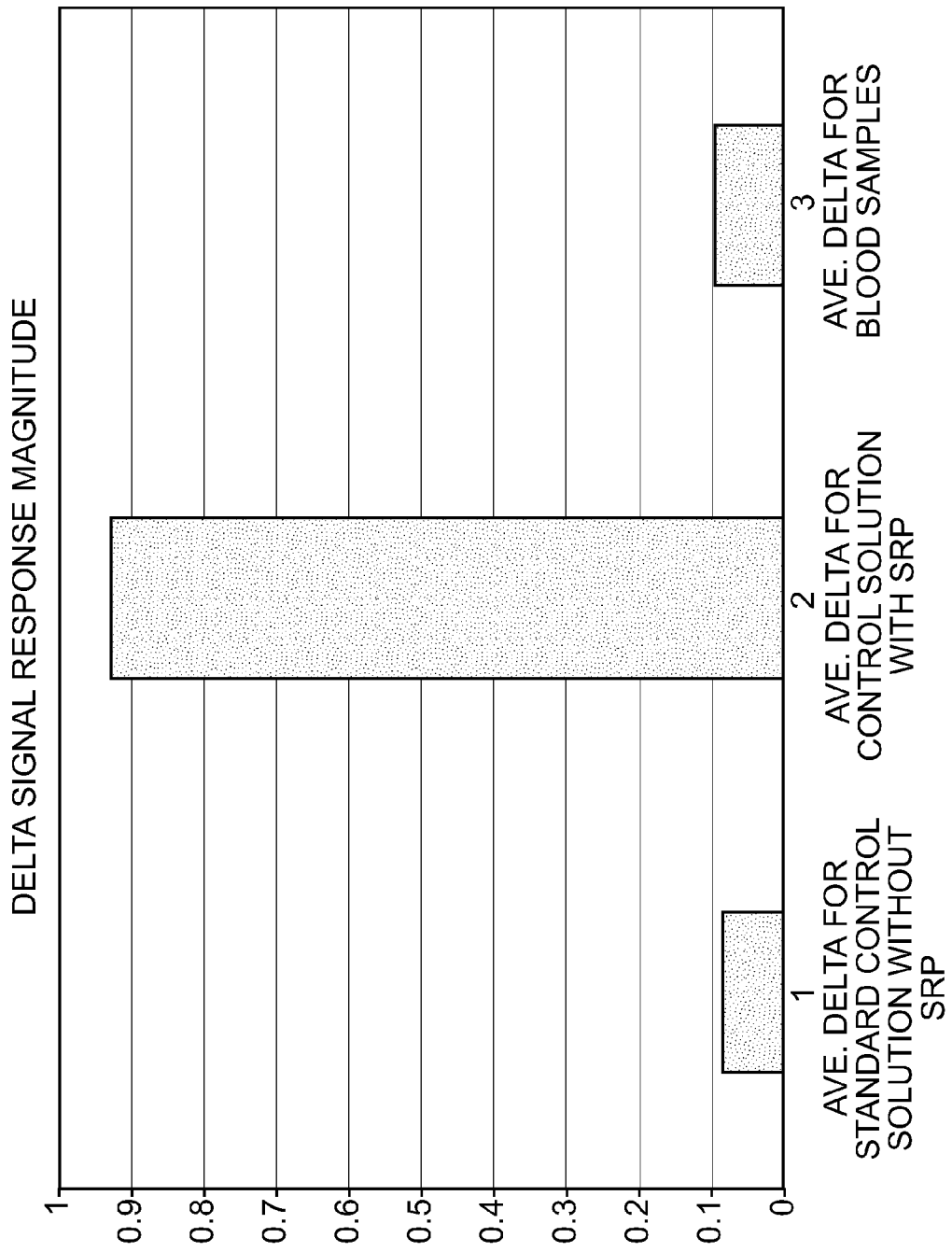
FIG. 9 is a graph depicting the difference in signal response magnitude with regard to three different samples.

As seen in Table 1 above and in FIG. 9, which depicts the values of table 1 on a bar graph, the difference signal for the control solution including the SRP component (also referred to the Automatic Control Solution "ACD") is of an entire order of magnitude larger than the samples without the SRP component. Therefore, the difference signal can be used in a simple logic circuit or routine to distinguish between a control solution and a true patient sample. For example, in the case of a blood glucose meter, the meter electronics could first be programmed to always administer a second voltage pulse of a predetermined duration in order to trigger oxidation or reduction of the SRP in a control solution, if present. Next, the meter could be programmed to perform the logic algorithm described above (either via digital programming or via analog circuit components) to calculate a difference signal or delta value. As noted above, a delta value that exceeds a predetermined threshold could be programmed to trigger the acknowledgement of a control calibration solution. In turn such an acknowledgement by the meter would prevent the control test data from being erroneously stored as an actual patient result.

The underlying meter could be programmed to alert the user to recognition of a control solution. For example, a graphical display could appear on the meter display. In addition, the meter could enter a query mode where the user must acknowledge the application of a control solution. As one example, the user could be alerted to the recognition of a control solution and be required to push a button, or provide some other input, to allow the meter to proceed.

While various substances are described as possible candidates for use as an SRP, they are not intended to be limiting of the claimed invention. Unless expressly noted, the particular substances are listed merely as examples and are not intended to be limiting of the invention as claimed.

In the foregoing disclosure, the measurement technique examined is multi-step chronoamperometry. However, there are other types of measurement that would be amenable to use in the invention. For example square wave voltammetry, differential pulse amperometry, and cyclic voltammetry are all contemplated to be viable means of measurement in the invention. It is not the intention to limit the scope of this invention to a particular measurement method.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for automatically distinguishing between a control solution having a known, predetermined concentration of an analyte and an actual patient/user sample in a biosensor comprising:
   a sample reception region;
   a reaction reagent system in said sample reception region comprising:
      an oxidation-reduction enzyme specific for the analyte;
      a first electron mediator capable of being reversibly reduced and oxidized; and
      a second electron mediator, capable of being reversibly reduced and oxidized, wherein the second electron mediator has a redox potential different from that of the first mediator; and
   a distinction system configured to detect the electro-chemical response signal produced by the reduction of the second electron mediator in order to identify a control solution.

2. The system of claim 1, wherein the control solution comprises the second electron mediator.

3. The system of claim 1, wherein the analyte is glucose.

4. The system of claim 1, wherein the second electron mediator does not interfere with the measurement of the analyte.

5. The system of claim 1, wherein the first electron mediator is a ruthenium containing material.

6. The system of claim 5, wherein the ruthenium containing material comprises hexaamine (III) trichloride.

7. The system of claim 1, wherein the second mediator is Ferrocene Dicarboxylic Acid.

8. The system of claim 1, wherein the second mediator is Ferrocenecarboxylic Acid.

9. The system of claim 1, wherein the second mediator is gentisic acid (2,5-dihydroxybenzoic acid).

10. The system of claim 1, wherein the second mediator is 2,3,4-trihydroxybenzoic acid.

11. The system of claim 1, wherein the second mediator is reduced in a potential range distinguishable from that of the first mediator.

12. The system of claim 1, wherein the second electron mediator is reduced at a potential having a magnitude at least 0.2 volts greater or less than that used to oxidize or reduce the first electron mediator.

13. The system of claim 1, wherein the distinction system comprises a meter configured to apply at least a first and a second electric pulse to the biosensor.

14. The system of claim 13, wherein the distinction system is configured to measure at least a first and a second current signal generated in response to at least the first and the second applied electric pulses.

15. The system of claim 13, wherein electric potentials of at least the first and the second applied electric pulses are of different magnitudes.

16. The system of claim 1, wherein the distinction system is configured to measure a hematocrit level of the control solution or the actual patient/user sample.

* * * * *

UNITED STATES PATENT AND TRADEMARK OFFICE
CERTIFICATE OF CORRECTION

PATENT NO. : 8,647,487 B2  
APPLICATION NO. : 13/025203  
DATED : February 11, 2014  
INVENTOR(S) : Natasha D. Popovich and Stephen G. Davies Page 1 of 1

It is certified that error appears in the above-identified patent and that said Letters Patent is hereby corrected as shown below:

Title page, item (57) in the Abstract, Line 3-4, "The solution is introduced into an electrochemical cell having a working and counter electrode." should read --The solution is introduced into an electrochemical cell having working and counter electrodes.--.

In the Claims:

Claim 1, Col. 15, Line 28, "mediator," should read as --mediator--.

Signed and Sealed this  
Tenth Day of June, 2014

Michelle K. Lee  
*Deputy Director of the United States Patent and Trademark Office*